United States Patent
Marliere et al.

(10) Patent No.: US 7,319,148 B2
(45) Date of Patent: Jan. 15, 2008

(54) COMBINATORIAL PRODUCTION OF NUCLEOTIDE AND NUCLEOSIDE (XITP) ANALOGUES

(75) Inventors: Philippe Marliere, Etiolles (FR); Sylvie Pochet, Paris (FR)

(73) Assignee: Institut Pasteur, Paris (FR)

( * ) Notice: Subject to any disclaimer, the term of this patent is extended or adjusted under 35 U.S.C. 154(b) by 221 days.

(21) Appl. No.: 10/297,999

(22) PCT Filed: Jun. 13, 2001

(86) PCT No.: PCT/FR01/01830

§ 371 (c)(1),
(2), (4) Date: Jun. 18, 2003

(87) PCT Pub. No.: WO01/96354

PCT Pub. Date: Dec. 20, 2001

(65) Prior Publication Data

US 2004/0023240 A1    Feb. 5, 2004

(30) Foreign Application Priority Data

Jun. 14, 2000 (FR) ................................. 00 07557

(51) Int. Cl.
C07D 215/38 (2006.01)
C07D 405/04 (2006.01)
(52) U.S. Cl. .................... 546/175; 548/517
(58) Field of Classification Search ............ 548/517; 546/175
See application file for complete search history.

(56) References Cited

OTHER PUBLICATIONS

Hoops et al., Template directed incorporation of nucleotide mixtures using azoe-nucleobase analogs, Nucleic Acids Research, 1997, vol. 25, No. 24, pp. 4866-4871.*

Sarafianos et al., Designing anti-AIDS drugs targeting the major mechanism of HIV-1 RT resistance to nucleoside analog drugs, The International Journal of Biochemistry & Cell Biology 36 (2004) 1706-1715.*

Sanger et al., PNAS USA, vol. 74, No. 12, pp. 5463-5467, Dec. 1977.*

Sonveaux, E., "Protecting Groups In Oligonucleotide Synthesis," Methods in Molecular Biology, vol. 26, Protocols for Oligonucleotide Conjugates, Ed. Agrawal S., 1994, Hamana Press Inc.*

J.T. Witkowski, "Design, Synthesis, and Broad Spectrum Antiviral Activity of 1-β-D-Ribofuranosyl-1,2,4-triazole-3-carboxamide and Related Nucleosides[1,2]" Journal of Medicinal Chemistry, vol. 15, No. 11, pp. 1150-1154, (1972).

M. Teresa Garcia-López, et al., "Studies of New Routes for the Synthesis of 4- and 5-Aminoimidazole Nucleoside Derivatives", J. Heterocyclic Chem., vol. 19, pp. 233-235, (1982).

T.P. Nedorezova, et al., "Effects of 4,5-disubstituted 1,2,3-triazoles and their N2-ribosides on pyrimidine precursors incorporation into nucleic acids of tumor cells", Chemical Abstracts, vol. 106:95702z, No. 13, (1987).

I.D. Shingarova, et al., "Nucleosides of 4-(methylthio)-1,2,3-triazole-5-carboxylic Acid Derivatives", Chemical Abstracts, vol. 108:6331d, No. 1, (1988).

I.D. Shingarova, et al., "Position of glycosidation of 5-substituted 4-chloro-1,2,3-triazoles", Chemical Abstracts, vol. 108:187169a, No. 21, (1988).

C. Le Bec, et al., "Derivatives of Imidazole-4-carboxamide as Substrates for Vairous DNA Polymerases", Nucleosides & Nucleotides, vol. 16, pp. 1301-1302, (1997).

Sylvie Pochet, et al., "Imidazole-4-Carboxamide and 1,2,4-Triazole-3-Carboxamide Deoxynucleotides as Simpliefied DNA Building Blocks with Ambiguous Pairing Capacity", Nucleosides & Nucleotides, vol. 17, pp. 2003-2009, (1998).

M. Sala, et al., "Ambiguous base pairing of the purine analogue 1-(2)-deoxy-β-D-ribofuranosyl)-imidazole-4-carboxamide during PCR", Nucleic Acids Research, vol. 24, pp. 3302-3306, (1996).

* cited by examiner

Primary Examiner—Rebecca Anderson
(74) Attorney, Agent, or Firm—Finnegan, Henderson, Farabow, Garrett & Dunner, L.L.P.

(57) ABSTRACT

The invention concerns novel nucleotide analogues comprising a reactive hydrazide function used as initial synthons for preparing compounds (formula I) capable of inducing mutations or capable of inhibiting a DNA polymerase or a kinase. The invention also concerns nucleic acids comprising said nucleotide and nucleoside analogues. Among such compounds, can be cited in particular the compound of formula (I)

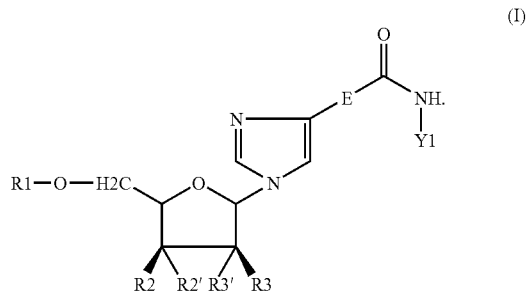

13 Claims, 2 Drawing Sheets

COMBINATORIAL PRODUCTION OF NUCLEOTIDE AND NUCLEOSIDE (XITP) ANALOGUES

This application is a 371 of PCT/FR01/01830 filed 13 Jun. 2001.

The invention concerns novel nucleotide analogues comprising a reactive hydrazide function (formula II) used as initial synthons for preparing compounds (formula I) capable of inducing mutations or capable of inhibiting a DNA polymerase or a kinase. The invention also concerns nucleic acids comprising said nucleotide and nucleoside analogues.

The nucleotide inhibitors currently available (acyclovir, gancyclovir, AZT, ddC, d4T, 3TC.) produce undesirable secondary effects in the case of prolonged treatment and repeated administrations. On the one hand, the intrinsic toxicity of these nucleotide analogues arises in particular from the fact that they can lack specificity vis-à-vis a polymerase or a given reverse transcriptase. On the other hand, after a certain period, the viruses become resistant to these inhibitors, even if the doses are increased.

The synthesis of new nucleotide inhibitors represents an important contribution towards renewing the methods of treatment of viral infections such as HIV, CMV and HSV. Hutchinson, 1990 shows that there are a number of difficulties linked to the synthesis of very large collections of modified nucleotides. For example, it appears necessary to protect the reactive functions of the bases or of the riboses with each addition or modification of groups.

The invention makes it possible to overcome these difficulties thanks to a basic synthon making it possible to obtain nucleotide or nucleoside analogues from a library in a single step. Thanks to these libraries, it is possible for example to screen highly specific HIV reverse transcriptase inhibitors.

The preparation of new nucleotides with ambiguous pairings, i.e. capable of being incorporated in the primer strand in response to more than one of the four bases A, C, G and T in the matrix strand, is also essential to perfect the mutagenesis processes (Sala et al., 1996; Zaccolo et al., 1996; Pochet et al., 1997). The ultimate mutagenic agent would consist of a DNA monomer which could pair with the four canonical bases at the stage of incorporation as triphosphate, then when it is copied as a matrix. The deoxynucleoside triphosphate of such an ambiguous base would make it possible to replace any canonical base by any of the three other three bases during replication by a DNA polymerase. Moreover, an in vivo hypermutagenesis process via the incorporation of the ambiguous base would simplify and accelerate the directed evolution protocols of the genes carried by plasmids, whilst avoiding the need for costly handling by erroneous PCR. A summary justifying the use of ambiguous bases in other applications can be found in the references Bergstrom et al., 1995; Loakes et al., 1995; Hill et al., 1998.

Moreover, the discovery of chemical structures which are simplified but endowed with the same capacities of one-to-one pairing as each of the four DNA bases, in other words A, C, G and T substitutes, makes possible the preparation of new probes or nucleic primers which can be used in various target nucleic acid amplification and detection techniques.

Moreover, it is possible to graft onto the initial synthon of formula II (see below), reactive molecules which are situated for example in the family of amino acids, which therefore makes it possible to functionalise the DNA.

Deoxynucleosides carrying a simplified purine in a simple imidazole nucleus substituted at positions 4 and 5 have been described in Pochet et al, 1998. These nucleosides are intrinsically capable of forming hydrogen bonds with the four canonical bases by rotation around the glycoside bond (syn and anticonformations) and the carboxamide bond ("A-like" and "G-like") (Pochet et al., 1995; Pochet et al., 1998). The incorporation of these nucleosides by the DNA polymerases (LeBec et al., 1997) and the mutagenic effects of their pairings are described in Sala et al., 1996; Pochet et al., 1997.

Within the scope of the present invention, variable lateral groups can be grafted to the simplified DNA monomer, hereafter designated $X_0$, via a carbohydrazide group. This initial synthon makes it possible to prepare multiple substrates of the DNA polymerases in one step. The carbohydrazide group constitutes a highly reactive function capable of condensing with any aldehyde or ketone. As many hydrazone derivatives, hereafter designated $X_1$, can therefore be formed from $X_0$. As many hydrazine derivatives, hereafter designated $X_2$, can be obtained by reduction of $X_1$.

Thus, the present invention relates to compounds of general formula I:

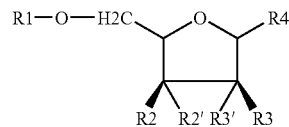

in which:
- the group R1 represents a hydrogen or a group chosen from the phosphate, diphosphate or triphosphate groups and the protective groups such as DMT.
- R2 and R2' are chosen independently from one another from H, OH, phosphoramidite and its derivatives, H-phosphonate and an elongation terminator T,R3 and R3' are chosen independently from one another from H, OH, the halogens (F, Br, Cl, I), a linear or branched alkyl group comprising 1 to 6 carbon atoms and an O—R5 group, R5 representing a linear or branched alkyl group comprising 1 to 6 carbon atoms,
- R4 represents a substituted heterocycle (symbolised by a circle), of formula

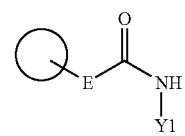

in which E designates a spacer arm made up of a saturated or unsaturated carbon chain of 0 to 20 carbon atoms, which may or may not comprise heteroatoms and/or is optionally substituted; said heterocycle being selected from:

a) the 5-atom heterocycles of formula:

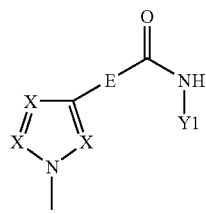

in which each X represents independently of the others a CH, C—R6 or N group, R6 being chosen from the halogens (F, Br, Cl, I), a linear or branched alkyl group comprising 1 to 6 carbon atoms and an O—R7 or S—R7 group, R7 representing a hydrogen or a linear or branched alkyl group comprising 1 to 6 carbon atoms, said heterocycles belonging in particular to the azole family, such as the rings

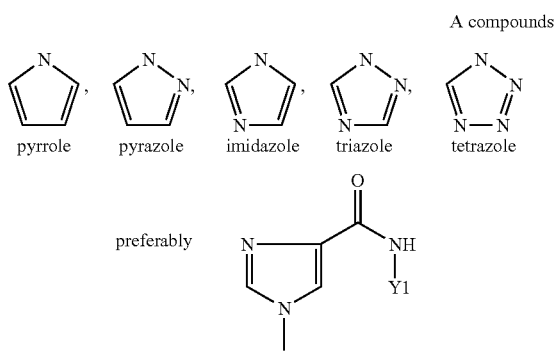

A compounds pyrrole    pyrazole    imidazole    triazole    tetrazole preferably b) 6-atom rings, in particular pyrimidines of formula

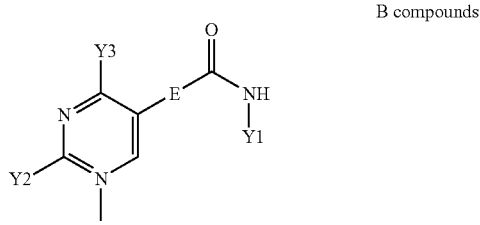

B compounds c) purine analogues of formula:

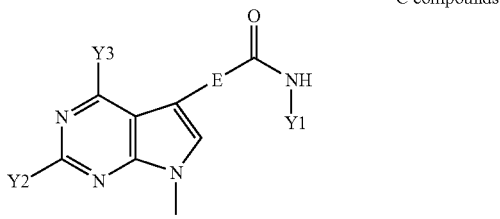

C compounds in which:

Y1 represents $NH_2$ (designated by the synthon $X_0$) or a:

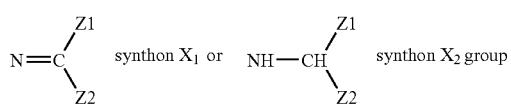

synthon $X_1$ or    synthon $X_2$ group

Y2 et Y3 are chosen independently from one another from H, OH, O, $NH_2$, the halogens (F, Br, Cl, I), $SCH_3$, SH, an amine, an amide (in direction —NH—CO—R) or a linear (direction —OR) or branched alkyl comprising 1 to 6 carbon atoms, Z1 and Z2 being chosen independently from one another from H and an organic group Concerning the terms "purines" and "pyrimidines", reference should be made to the definition given in the Oxford Dictionary of Biochemistry and Molecular Biology, Oxford Press, 1997. Examples of paths of synthesis of these compounds are described on pages 546 and 547 of this document.

Concerning the B compounds, the synthesis example presented in FIG. 2 is valid for nucleosides in the ribo and deoxy series and for phosphorylated derivatives. When X is $CONHNH_2$, a synthon $X_0$ is obtained according to the invention comprising a spacer arm $CH=CHCONH(CH2)n$, where n=6 in this example Among the synthons $X_0$, $X_1$ et $X_2$, the invention relates in particular to nucleoside analogues and nucleotide triphosphate analogues which will be designated $X_0TP$, $X_1TP$ and $X_2TP$. The nucleotide analogues according to the invention will preferably be used when the objective involves their incorporation in a nucleic acid. A nucleoside analogue according to the invention will preferably be used to inhibit a polymerase in situ in a cell, in particular for the manufacture of a medicament.

In compounds of formula I, the R1 group preferably represents a triphosphate group or a hydrogen according to the objective referred to above.

In the same way, according to the desired objective, at least one of the R2 and R2' groups can represent an OH group, which allows the continuation of the elongation by a polymerase or a terminator group T in the case of its being desirable to obtain polymerase inhibitors. Thus at least one of the R2 and R2' groups can represent the T group, which is preferably selected from F, Br, Cl, I, $N_3$, and a linear or branched alkyl group comprising 1 to 6 carbon atoms. Of course, any equivalent group functioning as an elongation terminator is intended for the preparation of compound inhibiting retrovirus reverse transcriptases.

Advantageously, when Y1 is $NH_2$, a subject of the invention is the initial synthons of general formula II (synthon Xo ):

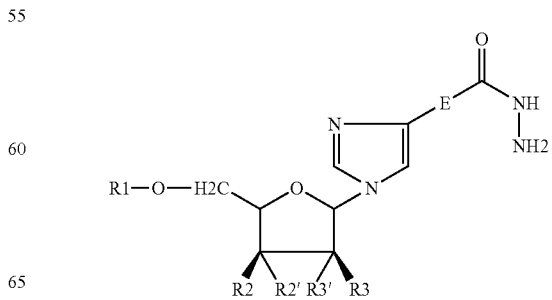

in which R1, R2, R2', R3, R3' and E correspond to the groups of formula I. Among such compounds, the invention relates in particular to the compound called dXoTP in which R1 is a triphosphate group, and R3 and R3' represent H, The compounds of formula II explained above can be used as initial synthon for the preparation of a library of nucleotide and/or nucleoside analogues. Their carbohydrazide group in effect makes it possible to conjugate these compounds in a single step with any molecule comprising an aldehyde or ketone function giving $X_1$ synthons after condensation or $X_2$ after reduction.

By condensation of the compounds of formula II (synthons $X_0$ and $X_0TP$) with any molecule comprising an aldehyde or ketone function, a compound of formula I is obtained, in which the group Y1 represents general formula:

Z1 and Z2 representing independently from one another a hydrogen or an organic group. These compounds will be designated $X_1TP$ (nucleotide triphosphate analogues) or $X_1$ (nucleoside analogues).

It is possible to reduce such compounds and obtain compounds of formula I (synthons $X_2$ and $X_2TP$) in which the Y1 group represents general formula:

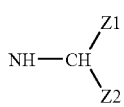

For example, compounds can be cited in which at least one of the Z1 and Z2 groups is selected from the aromatic groups, in particular from the groups of formula:

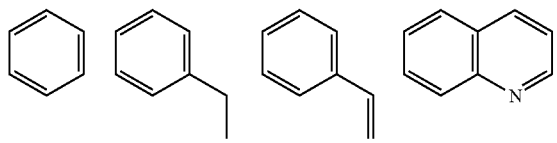

-continued

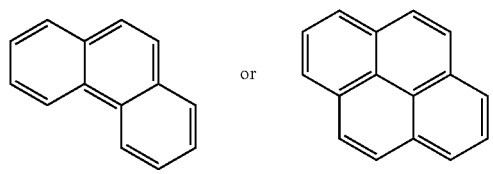

At least one of the Z1 and Z2 groups can also be selected from the thiol, alkyl, carbonyl, amine, alcohol, aryl, and amino acid groups.

From another perspective, the compounds of the invention can be characterised in that Z1 or Z2 forms a ring with Y3.

In a particular embodiment, the invention concerns the above-mentioned compounds in which Z1 or Z2 comprises a fluorescent or phosphorescent marker, in particular fluorescamine or fluorescein. For example, the fluorescamine can be reacted to mark the compound or to detect its presence within a nucleic acid.

Compounds can therefore be prepared with a spacer arm and a marker, for example a compound of formula:

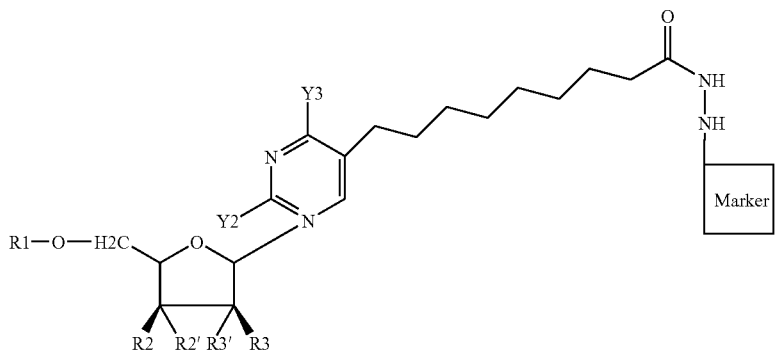

Advantageously, the abovementioned compounds are substrates of a polymerase and can form pairings with natural bases, of a reverse transcriptase and/or a nucleotide kinase.

Moreover, said compounds can introduce mutations into a nucleic acid or block the synthesis of DNA or RNA, in particular by the DNA polymerases, the retrovirus reverse transcriptases and kinases. Among the kinases, any kinase is meant which is capable of phosphorylating mono- or di-phosphate nucleotides in vivo or in vitro. More particularly, the deoxycytidine kinases, in particular the human DCK2 described in U.S. Pat. No. 5,914,258, the deoxyguanosine kinases and the thymidine kinases.

Thus, a compound according to the invention in which Y1 is $NH_2$ can be used as an initial synthon for the preparation of libraries of nucleotide and/or nucleoside analogues and, of said analogues, those which can induce mutations and/or block the synthesis of DNA or RNA can be identified.

The invention also relates to a method for the preparation of compounds of general formula II described above, characterised in that it includes the following steps:
a) preparation of the nucleoside having for heterocycle a 5-atom heterocycle of formula:

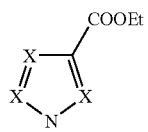

in which X represents independently from one another a CH, C—R6 or N group, R6 being chosen from the halogens (F, Br, Cl, I), a linear or branched alkyl group comprising 1 to 6 carbon atoms and an O—R7 or S—R7 group, R7 representing a linear or branched alkyl group comprising 1 to 6 carbon atoms, said heterocycles belonging in particular to the azole family, such as the

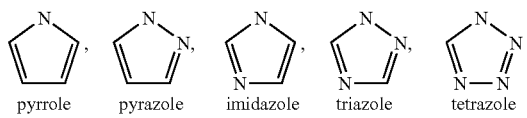

rings
b) protection of the 5'alcohol and conversion of the ethyl ester function into a carbohydrazide function by the action of hydrazine,
c) protection of the amine function of the carbohydrazide group by a protective group such as the benzyloxycarbonyl group, acetylation of the alcohol in position 3',
d) phosphorylation after deprotection of the alcohol in position 5',
e) and hydrogenolysis of the benzyloxycarbonyl group.

Step a) is preferably is carried out by means of an N-transdeoxyribosylase in the case of deoxyribose and step d) consists of the phosphorylation of the nucleoside by cyanoethyl phosphate in the presence of dicyclohexylcarbodiimide; concomitant release in a basic medium of the alcohol in position 3' and of the cyanoethyl group of the 5' phosphate; then condensation of pyrophosphate to 5' activated phosphate in the form of morpholidate.

From the compounds of general formulae II, it is possible to prepare a compound of general formula I described above, by condensation of a compound of general formula II with an aldehyde or a ketone, optionally followed by a reduction.

It is possible to react one or more compound(s) of general formula II with a library of aldehydes and/or ketones, optionally followed by a reduction, so as to obtain a library of compounds of formula I.

The synthesis path described in FIG. 1 illustrates a particular embodiment of the process according to the invention. The ethyl ester of imidazole-4-carboxylic acid was converted into its deoxynucleoside by the action of N-transdeoxyribosylase, used without purification in the form of a protein extract of *Lactobacillus leichmannii*, taking thymidine as a source of deoxyribose. After protection of the alcohol in position 5' by a dimethoxytrityl group, the nucleoside carrying the ethyl ester function was in turn converted into its carbohydrazide derivative by the action of hydrazine. The amine function of the carbohydrazide group was then protected by condensation of a benzyloxycarbonyl group. After acetylation of the alcohol in position 3' and release of the alcohol in position 5', the synthon obtained was subjected to the following phosphorylation steps, namely: phosphorylation by cyanoethyl phosphate in the presence of dicyclohexylcarbodiimide; concomitant release in a basic medium of the alcohol in position 3' and of the 5' phosphate; condensation of pyrophosphate to 5' activated phosphate in the form of morpholidate. The manufacture of the reactive synthon deoxynucleoside triphosphate of the carbohydrazide $dX_0TP$ was achieved by hydrogenolysis of the benzyloxycarbonyl group.

Condensation of the $dX_0TP$ carbohydrazide with Z1-CHO and Z1-CO-Z2 leads to the $dX_1TP$ hydrazone derivatives, then to the $dX_2TP$ compounds after reduction.

An other aspect of the invention relates to compounds which can be obtained using the methods explained above, and to the libraries of compounds of general formula I which can be obtained when one or more compounds of general formula II are reacted with a library of aldehydes and/or ketones.

The invention also concerns a method for identification of compounds capable of introducing a mutation into a nucleic acid comprising the steps consisting of i) incorporating into a synthetic oligonucleotide, a compound of formula I in which Y1 is $NH_2$, ii) reacting said compound by condensation with at least one aldehyde and/or ketone, optionally followed by a reduction, iii) replicating said oligonucleotide using a polymerase and determining whether a mutation has been introduced into the newly synthesised strand.

Thus, in another embodiment, the invention relates to a method of localised mutation of a nucleic acid characterised in that i) a synthetic oligonucleotide is prepared, comprising at least one compound according to the invention, ii) said oligonucleotide is replicated using a polymerase.

In another alternative, the invention relates to a method for random mutation of a nucleic acid comprising the steps consisting of using a reaction mixture comprising at least one abovementioned compound for the amplification of a nucleic acid.

Such a process of random mutagenesis is particularly useful for modifying the activity of a significant polypeptide.

For elongation, replication and amplification, it is possible to use an exo– DNA polymerase, such as for example Taq polymerase, Klenow fragment and Vent polymerase.

However, it is possible to use exo+ DNA polymerase in the case of its being desirable to screen the compounds according to the invention, which would be resistant to exonuclease activity. Such compounds are particularly useful in mutation detection processes.

An additional aspect concerns a method for identification of a compound capable of inhibiting an enzyme selected from a polymerase, in particular a reverse transcriptase and/or a kinase, in particular any kinase capable of phosphorylating mono- or di-phosphate nucleotides in vivo or in vitro (deoxycytidine kinases, deoxyguanosine kinases and thymidine kinases) characterised in that the activity of said enzyme is tested in the presence of at least one compound according to the invention.

In this method, it is possible to test the effect of at least one of said compounds on cells infected by a retrovirus, said compound being found in the form of a nucleoside analogue. Nucleosides can in fact cross the membrane of the cells, which is not the case with nucleotides, due to the negative charge of the phosphate groups.

Large-scale screening can therefore be carried out, using a library according to the invention and an iterative process with fractions of the library, via routine experiments, leads to the identification of one or more compound(s) blocking the replication of the viruses.

The invention relates to the compounds that can be obtained using the abovementioned method.

Moreover, the compounds of the invention can be used in primers or probes for the amplification and/or detection of a target nucleic acid.

A "probe" or "primer" is defined, within the meaning of the invention, as being a nucleotide fragment comprising for example from 10 to 100, in particular from 15 to 35 natural or modified nucleotides, comprising at least one compound corresponding to formula I described above and possessing a hybridisation specificity in determined conditions to form a hybridisation complex with a target nucleic acid. The probes according to the invention, whether specific or non-specific, can be immobilised, directly or indirectly on a solid support; they are then referred to as "captive probes". Moreover, said probes can carry a marker agent allowing their detection; they are then referred to as "detection probes".

A "captive probe" is immobilised or immobilisable on a solid support by any appropriate means, for example by covalence, by adsorption or by direct synthesis on a solid support. These techniques are in particular described in the patent application WO 92/10092. The most general method consists of immobilising the nucleic acid extracted from the cells of different tissues or from culture cells on a support (such as nitrocellulose, nylon™, polystyrene) and incubating, under well-defined conditions, the target nucleic acid immobilised with the probe. After hybridisation, the surplus probe is eliminated and the hybrid molecules formed are detected using the appropriate method (measurement of radioactivity, fluorescence or enzyme activity connected with the probe).

A "detection probe" can be marked by means of a marker chosen for example from the radioactive isotopes, enzymes, in particular enzymes capable of acting on a chromogenic, fluorigenic or luminescent substrate, (in particular a peroxidase or an alkaline phosphatase), chromophoric chemical compounds, chromogenic, fluorigenic or luminescent compounds, nucleotide base analogues and ligands such as biotin. The marking of the primers or probes obtained according to the invention is carried out by radioactive elements or non-radioactive molecules. The non-radioactive entities are selected from ligands such as biotin, avidin, streptavidin, dioxigenin, haptens, colouring agents, luminescent agents such as radioluminescent, chemiluminescent, bioluminescent, fluorescent (fluorescein isothiocyanate FITC, R-phycoerythrine PE, Quantum Red™, SIGMA and fluorescamine, Molecular Bioprobes) and phosphorescent agents.

In a particular embodiment, the invention relates to the marked compounds of formula I. As indicated above, a compound of formula II can be condensed with a molecule comprising an aldehyde or ketone function. In this case, said molecules carry a chromophoric type marker, chromogenic, fluorogenic or luminescent compounds or ligands such as biotin.

The nucleic acids comprising at least one compound of formula I are a subject of the present invention. They can be utilised in PCR type techniques (Erlich, 1989; Innis et al., 1990, and Rolfs et al., 1991). This technique necessitates the choice of pairs of oligonucleotide primers framing the fragment to be amplified. For example, reference can be made to the technique described in the American patent U.S. Pat. No. 4,683,202. Other amplification techniques can be advantageously used as an alternative to PCR (PCR-like) with the help of primer pairs according to the invention. The term "PCR-like" is intended to designate all the methods using direct or indirect reproductions of nucleic acid sequences, or in which the marking systems have been amplified, these techniques are well known to the person skilled in the art.

The invention also concerns a kit for the amplification and/or detection of a target nucleic acid and a pharmaceutical composition comprising a compound according to the invention or a nucleic acid according to the invention. It also relates to the use of a nucleic acid described above as ribozyme. The term "ribozyme", within the meaning of the invention, refers to a nucleic acid, a nucleic acid derivative or a chemical hybrid between nucleic acid and peptide which has catalytic properties, or properties of modulation of the activity or expression of a protein, a polypeptide, a peptide or a gene. A nucleic acid according to the invention can therefore be substituted for an enzyme.

From another perspective, the invention relates to antisense oligonucleotides comprising at least one compound of formula I. The term "antisense" is meant to designate a complementary oligonucleotide of a target DNA or RNA blocking transcription or translation. Examples of use are given in particular in WO9954463, WO9838204, WO9829448, WO9735960, WO9710840 et WO9625497.

Hence, said nucleic acid according to the invention is useful as a medicament and in treatment methods.

The invention also relates to the use of a compound described above for the manufacture of a medicament, in particular for the manufacture of a medicament intended for the treatment of retroviral infections and cancer.

EXAMPLE 1

Figure 1:
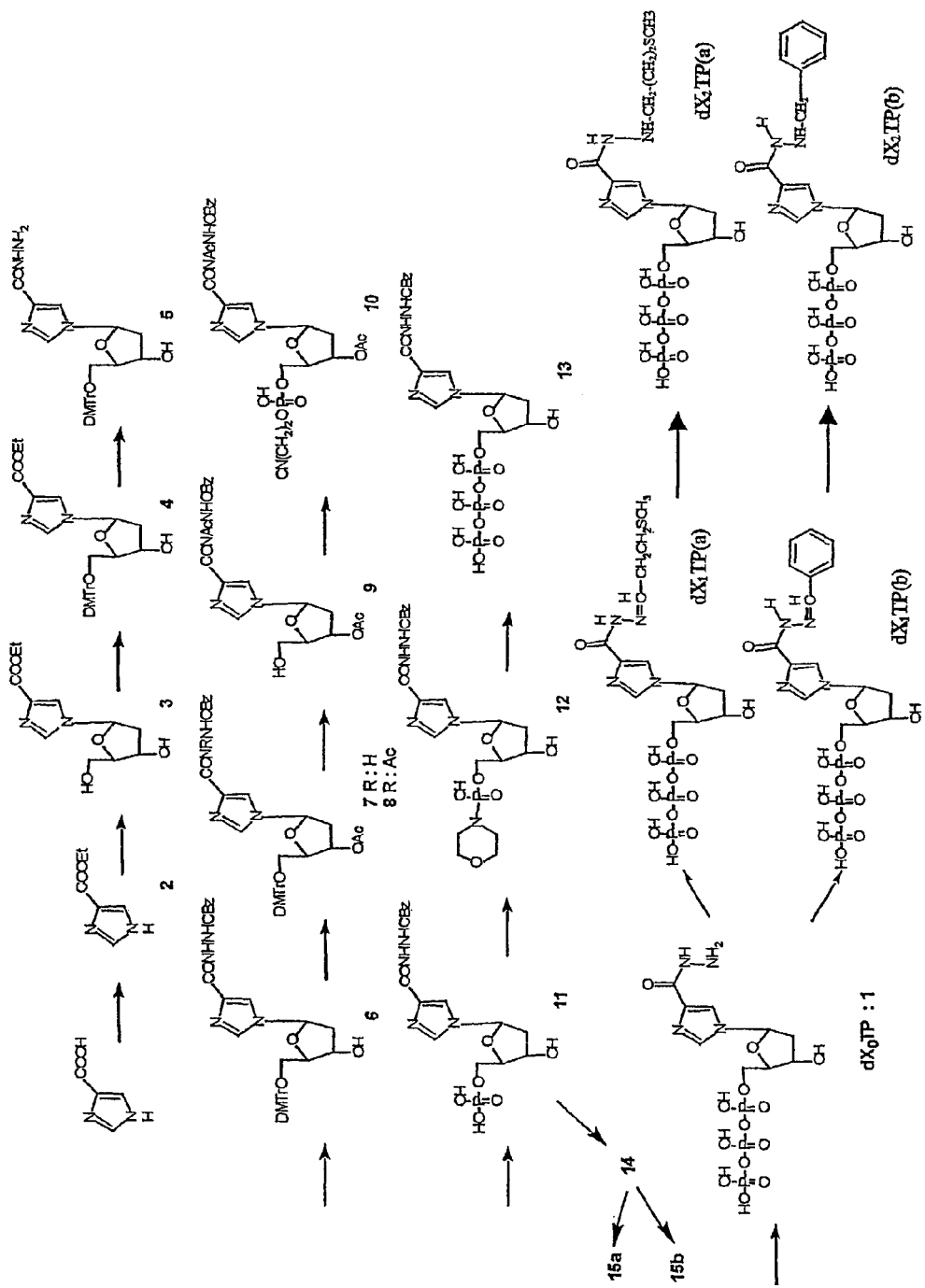
FIG. 1 illustrates a particular embodiment of the process according to the invention, which is described in the Examples.
Figure 2:
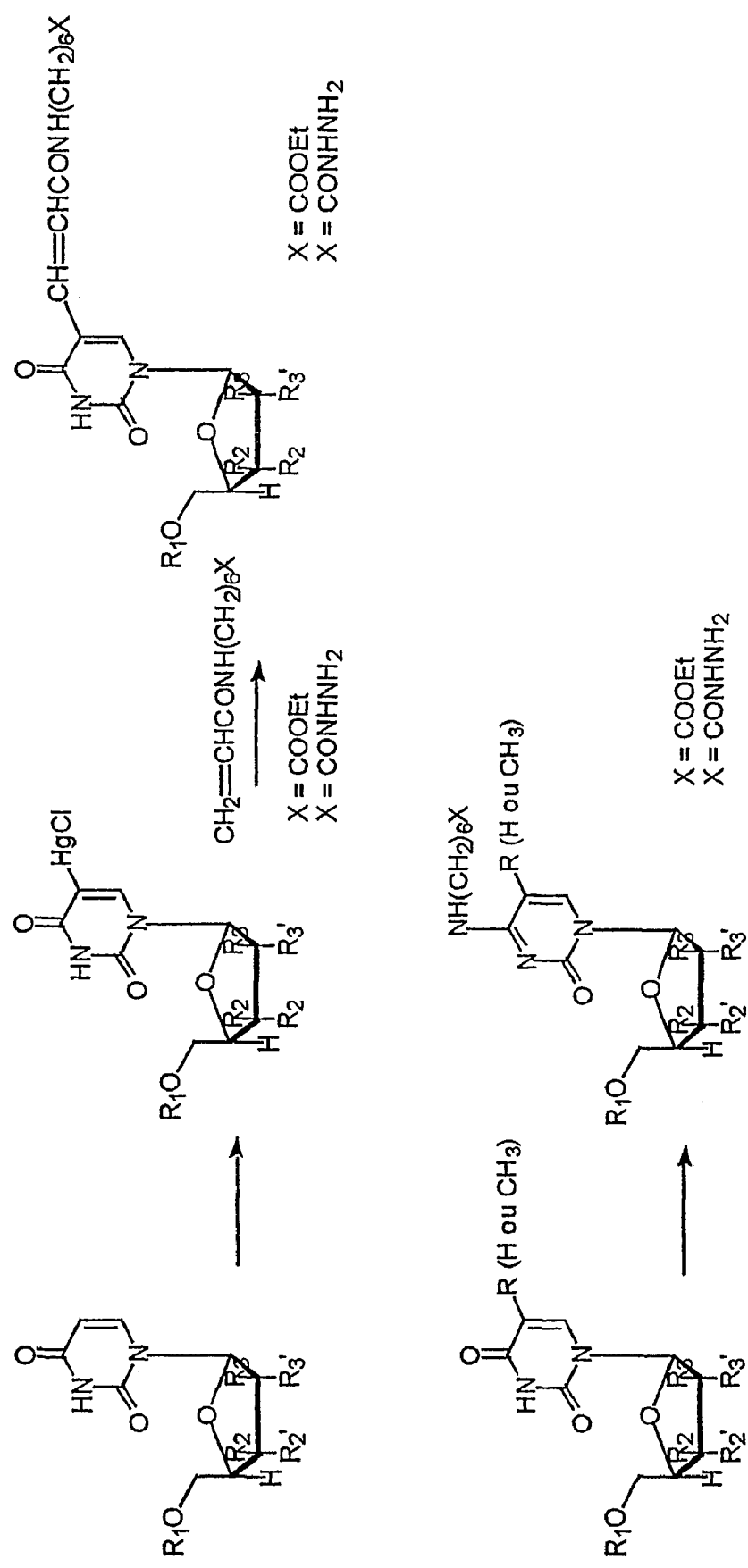
FIG. 2 illustrates a particular embodiment of the process according to the invention consisting of the synthesis of nucleosides in the ribo and deoxy series and phosphorylated derivatives. When X is $CONHNH_2$, a synthon $X_0$ is obtained comprising a spacer arm $CH\!-\!CHCONH(CH_2)_n$, where $n=6$.

Method for Preparation of Preferred Compounds According to the Invention (FIG. 1).

The synthesis of triphosphate 1 involves the introduction of a temporary protective group on the hydrazine function which can be released in these neutral conditions. For this purpose, the benzyloxycarbonyl group was selected. The triphosphate chain was introduced in 3 steps, in accordance with the procedures described by Tener and Moffatt. The nucleoside 3 was obtained from compound 2 by enzymatic transglycosylation using N-deoxyribosyltransferase as previously described by Pochet et al. 1995.

5'-dimethoxytritylation of compound 3 in pyridine made it possible to obtain compound 4 with a yield of 73%. The treatment of compound 4 with a large surplus of hydrazine hydrate at 60° C. led to compound 5 which can be used in the following stages without additional purification.

The benzyloxycarbonyl group was introduced by reacting compound 5 with benzyloxycarbonylsuccinimidate leading to compound 6 with a yield of 81%. Acylation with acetic anhydride in pyridine produced a mixture of two major compounds corresponding to the 3'-O-acetylated compound 7 (24%) and the 3'-O,N-diacetylated compound 8 (38%). Complete acetylation was rapidly obtained in acetonitrile using acetic anhydride (2.2 eq.) in the presence of triethylamine catalysed by DMAP making it possible to obtain compound 8 with a yield of 80%. After detritylation of compound 8, condensation of compound 9 with cyanoethylphosphate in pyridine in the presence of DCC, followed by treatment with a solution of 2% sodium methylate in methanol, the process led to the 5'monophosphate compound 11 (52%). The triphosphate compound 13 was obtained in two steps, via the morpholidate compound 12 with a yield of 50%. Suppression of the protective benzyloxycarbonyl group was achieved by hydrogenolysis on Pd/C in the presence of $H_2$. Thus, the treatment of compounds 11 and 13 made it possible to obtain the monophosphate 14 and triphosphate 1 derivatives.

EXAMPLE 2

Condensation of the Compound 1 with Aldehydes.

Derivatisation of the hydrazine function was carried out using aromatic and aliphatic aldehydes: firstly, the monophosphate compound 14 was treated with 3-methylthiopropionaldehyde and benzaldehyde in $H_2O$/methanol to give the compounds 15a and 15b. These products were isolated by reversed phase HPLC and were characterised by the mass spectrometry technique and by NMR. In the same way, compound 1 in TEAA buffer (pH 7,5) was treated at 4° C. with a surplus of aldehydes in methanol to give compounds 16a and 16b. The structure of the triphosphate derivatives was confirmed by mass spectrometry.

To compound 1 in 0.2 ml of 0.1M TEAA was added an aldehyde (25 μL in 0.1 mL of methanol). After 2 hours, the solution was concentrated and purified by HPLC at λ=230 nm (0 to 25% acetronitrile in 10 mM TEAA). The fractions containing the pure product were lyophilised and passed through a cation-exchange column (Dowex) to give triphosphates in the form of sodium salts.

EXAMPLE 3

Incorporation of $dX_0TP$ and $dX_1TP$ Analogues in the Nucleic Acids.

The analogues ($dX_0TP$, $dX_1TP(a)$ and $dX_1TP(b)$) were subjected to primer elongation experiments catalysed by the exo– Klenow fragment. A primer was marked at its 5' end by reaction of a $[\gamma-^{32}P]ATP$ using T4 polynucleotide kinase. The appropriate matrices and the marked primers were incubated at 75° C. for 15 minutes, then cooled slowly at ambient temperature for 1 hour. In different reaction mixtures, elongation of the primer was carried out with a DNA polymerase in the presence of the given $dX_1TPs$. The samples were then denatured then loaded on a polyacrylamide gel (20% 7M urea). After electrophoresis, the gels were visualised by autoradiography using a Phosporimager™.

REFERENCES

Bergstrom D. E., Zhang P., Toma P. H., Andrews P. C. & Nichols R. (1995) "Synthesis, structure, and deoxyribonucleic acid sequencing with a universal nucleoside: 1-(2'-deoxy-β-D-ribofuranosyl)-3-nitropyrrole" J. Am. Chem. Soc. 117, 1201-1209.

Hill F., Loakes D. & Brown D. M. (1998) "Polymerase recognition of synthetic oligonucleotides incorporating degenerate pyrimidine and purine bases" Proc. Nat. Acad. Sci., 95, 4258-4263.

Hutchinson D. W. (1990) TIBTECH, 8, 348-353.

Le Bec C., Roux P., Buc H. & Pochet S. (1997) Derivatives of imidazole-4-carboxamide as substrates for various DNA polymerases. Nucleosides & Nucleotides 16 (7-9), 1301-1302.

Loakes D., Brown D. M., Linde S. & Hill F. (1995) "3-Nitropyrrole and 5-nitroindole as universal bases in primers for DNA sequencing and PCR" Nucleic Acids Research 23, 2361-2366.

Pochet S., Dugué L., Meier A. & Marlière P. (1995) "Enzymatic synthesis of 1-(2-deoxy-β-D-ribofuranosyl)-imidazole-4-carboxamide, a simplified DNA building block" Bioorganic & Medicinal Chemistry Letters 5, 1679-1684.

Pochet S., Dugué L., Sala M., Pezo V. & Wain-Hobson S. (1997) "Ambiguous base pairing of the purine analogue 1-(2-deoxy-β-D-ribofuranosyl)-imidazole-4-carboxamide during PCR" Nucleosides & Nucleotides 16 (7-9), 1749-1752.

Pochet S. & Dugué L. (1998) "Imidazole-4-carboxamide and triazole-4-carboxamide deoxynucleosides as simplified DNA building-blocks with ambiguous base pairing capacity" Nucleosides & Nucleotides 17(9-11), 2003-2009.

Sala M., Pezo V., Pochet S. & Wain-Hobson S. (1996) "Ambiguous base pairing of the purine analogue 1-(2-deoxy-β-D-ribofuranosyl)-imidazole-4-carboxamide during PCR" Nucleic Acids Research 24, 3302-3306.

Zaccolo M., Williams D. M., Brown D. M. & Gherardi E. (1996) "An approach to random mutagenesis of DNA using mixtures of triphosphate derivatives of analogues" J. Mol. Biol. 255, 589-603.

What is claimed is:

1. A compound of the formula:

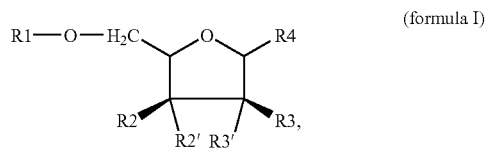

(formula I)

wherein:

R1 is H, a phosphate group, a diphosphate group, a triphosphate group, or DMT;

R2 and R2' are independently selected from H, OH, a phosphoramidite, H-phosphonate, F, Br, Cl, I, $N_3$, and a linear or branched alkyl group consisting of 1 to 6 carbon atoms;

R3 and R3' are independently selected from H, OH, a halogen (F, Br, Cl, I), a linear or branched alkyl group consisting of 1 to 6 carbon atoms, and an O—R5 group, wherein R5 is a linear or branched alkyl group consisting of 1 to 6 carbon atoms;

R4 is a substituted heterocycle of the formula:

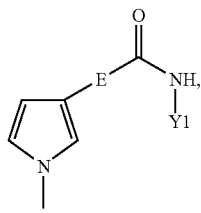

wherein:

E is a spacer arm of 0 to 20 saturated or unsaturated carbon atoms, wherein from 1 to 20 of the carbon atoms are optionally heteroatoms and/or are optionally substituted;

wherein:

Y1 is $NH_2$ (designated by the synthon X0),

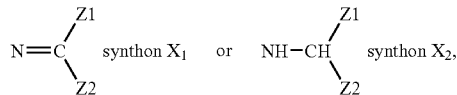

wherein Z1 and Z2 are independently selected from hydrogen, a thiol, an alkyl, a carbonyl, an amine, an alcohol, an aryl, fluorescamine and fluorescein.

2. The compound according to claim 1, wherein R1 is a triphosphate group.

3. The compound according to claim 1, wherein R1 is H and R2' is OH.

4. The compound according to claim 1, wherein R2 and R2' are independently selected from F, Br, Cl, I, $N_3$, and a linear or branched alkyl group consisting of 1 to 6 carbon atoms.

5. The compound according to claim 1, wherein Y1 is:

wherein Z1 and Z2 are independently selected from hydrogen, an aromatic, a thiol, an alkyl, a carbonyl, an amine, an alcohol, an aryl, fluorescamine and fluorescein.

6. The compound according to claim 1, wherein Y1 is:

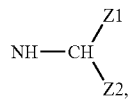

wherein Z1 and Z2 are independently selected from hydrogen, an aromatic, a thiol, an alkyl, a carbonyl, an amine, an alcohol, an aryl, fluorescamine and fluorescein.

7. The compound according to claim 1, wherein Y1 is synthon $X_1$ or synthon $X_2$ and at least one of groups Z1 and Z2 is an aromatic group of formula:

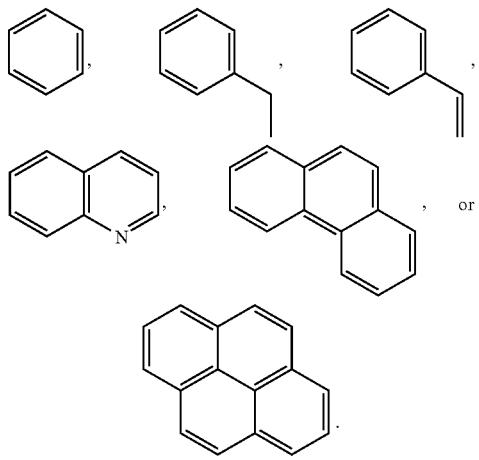

8. The compound according to claim 1, wherein Y1 is synthon $X_1$ or synthon $X_2$ and at least one of groups Z1 and Z2 is a thiol, alkyl, carbonyl, amine, alcohol, or aryl.

9. The compound according to claim 1, wherein Y1 is synthon $X_1$ or synthon $X_2$ and Z1 or Z2 is a fluorescamine or fluoresceine marker.

10. The compound according to claim 1, wherein R1 is DMT.

11. The compound according to claim 1, wherein Z1 is H and Z2 is H.

12. The compound according to claim 1, wherein R1 is H.

13. The compound according to claim 1, wherein R2' is OH.

* * * * *

UNITED STATES PATENT AND TRADEMARK OFFICE
CERTIFICATE OF CORRECTION

PATENT NO. : 7,319,148 B2
APPLICATION NO. : 10/297999
DATED : January 25, 2008
INVENTOR(S) : Philippe Marliere and Sylvie Pochet It is certified that error appears in the above-identified patent and that said Letters Patent is hereby corrected as shown below:

Title page, (73) Assignee: Institut Pasteur, Paris, (FR), should read

--(73) Assignees: Institut Pasteur, Centre National De La Recherche Scientifique (CNRS), both of Paris, (FR)--

Signed and Sealed this

Fourteenth Day of September, 2010

David J. Kappos
*Director of the United States Patent and Trademark Office*

UNITED STATES PATENT AND TRADEMARK OFFICE
CERTIFICATE OF CORRECTION

PATENT NO.        : 7,319,148 B2
APPLICATION NO.   : 10/297999
DATED             : January 15, 2008
INVENTOR(S)       : Philippe Marliere and Sylvie Pochet It is certified that error appears in the above-identified patent and that said Letters Patent is hereby corrected as shown below:

Title page, (73) Assignee: Institut Pasteur, Paris, (FR), should read

--(73) Assignees: Institut Pasteur, Centre National De La Recherche Scientifique (CNRS), both of Paris, (FR)--

This certificate supersedes the Certificate of Correction issued September 14, 2010.

Signed and Sealed this
First Day of February, 2011

David J. Kappos
*Director of the United States Patent and Trademark Office*